United States Patent [19]

Miyazawa et al.

[11] Patent Number: 5,128,252
[45] Date of Patent: Jul. 7, 1992

[54] PROCESS FOR PRODUCING OPTICALLY ACTIVE COMPOUND

[75] Inventors: Kazutoshi Miyazawa; Naoyuki Yoshida, both of Ichihara, Japan

[73] Assignee: Chisso Corporation, Tokyo, Japan

[21] Appl. No.: 690,256

[22] Filed: Apr. 25, 1991

Related U.S. Application Data

[62] Division of Ser. No. 476,546, Feb. 6, 1990.

[30] Foreign Application Priority Data

Feb. 21, 1989 [JP] Japan .................. 1-39297

[51] Int. Cl.$^5$ .................. C12P 7/62; C12P 7/64; C07P 41/00; C12N 9/20
[52] U.S. Cl. .................. 435/134; 435/135; 435/136; 435/155; 435/198; 435/280; 560/179; 560/185
[58] Field of Search .......... 435/135, 280, 155, 198, 435/134, 136; 560/179, 185

[56] References Cited

U.S. PATENT DOCUMENTS

| 4,272,437 | 6/1981 | Menard et al. | 260/239 |
|---|---|---|---|
| 4,472,503 | 9/1984 | Matsuo et al. | 435/198 |
| 4,719,178 | 1/1988 | Macrae et al. | 435/134 |
| 4,735,900 | 4/1988 | Urata et al. | 435/134 |
| 4,839,287 | 6/1989 | Holmberg et al. | 435/134 |
| 4,882,451 | 11/1989 | Yoshida et al. | 435/280 |
| 4,940,845 | 7/1990 | Hirota et al. | 435/134 |
| 4,962,031 | 10/1990 | Yoshida et al. | 435/155 |
| 4,963,492 | 10/1990 | Keller et al. | 435/155 |
| 4,971,909 | 11/1990 | Kaneoya et al. | 435/280 |
| 4,985,358 | 1/1991 | Sawamura et al. | 435/134 |
| 4,996,158 | 2/1991 | Oda et al. | 435/280 |

FOREIGN PATENT DOCUMENTS

| 0231089 | 8/1987 | European Pat. Off. | 435/135 |
|---|---|---|---|
| 0266217 | 5/1988 | European Pat. Off. | 435/135 |
| 0288994 | 11/1988 | European Pat. Off. | 435/135 |
| 0417823 | 3/1991 | European Pat. Off. | 435/134 |
| 2119397 | 11/1983 | United Kingdom | 435/134 |

OTHER PUBLICATIONS

Seebach et al., Liebig's Ann. Chem., 1976, pp. 1357–1369.

*Primary Examiner*—Herbert J. Lilling
*Attorney, Agent, or Firm*—Wenderoth, Lind & Ponack

[57] ABSTRACT

The invention provides an optically active compound which is R- or S- ester having the general formula:

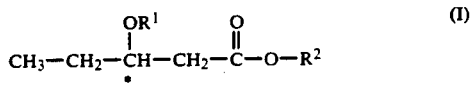

(I)

wherein $R^1$ is hydrogen or acyl of 2–20 carbon atoms, $R^2$ is alkyl, alkenyl or alkynyl of 3–40 carbon atoms, and the carbon indicated by * is an asymmetric carbon atom.

5 Claims, No Drawings

PROCESS FOR PRODUCING OPTICALLY ACTIVE COMPOUND

This application is a division of application Ser. No. 07/476,546, filed Feb. 7, 1990.

BACKGROUND OF THE INVENTION

The present invention relates to optically active compounds which are useful as starting materials for physiological active materials, functional materials and the like, and as intermediates. However, as the compounds have optical isomers, and in practical uses, it is necessary to use only one of these antipodes. Further, when racemates or compounds having low optical purity are used, the obtained compounds apparently do not develop enough physiological activity or functionality.

In order to obtain an optically active substance, it is necessary to conduct an asymmetric synthesis, to optically resolve a recemate (itself typically obtained by a synthetic chemical technique), or to convert from an optically active starting material by a stereochemical synthetic method. In many cases, the process is troublesome and disadvantageous industrially, and scarce materials should be used.

Accordingly, it is desired to develop a technique for obtaining optically active compounds by an industrially advantageous method.

As ester of 3-hydroxypentanoic acid, methyl 3-hydroxypentanate and ethyl 3-hydroxypentanate are known. Both of them have low optical purity and the operation process is troublesome. Even if the process can be used experimentally, it is unable to use the process industrially.

For example, G. Frater reported a method in which ethyl R-3-hydroxypentanate is obtained by asymmetric reduction of ethyl 3-ketopentanate with baker's yeast. The method has the following disadvantages (G. Frater, Helv. Chim. Acta, 62, 2829(1979)).

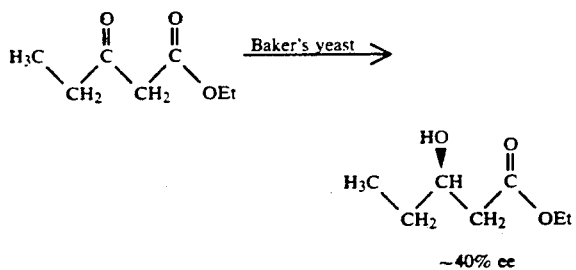

(1) The product has low optical purity and can not be used as a physiological substance or a starting material of a functional compound. According to our determination, the purity is about 40% ee.

(2) Since the concentration of substrate is low in a reaction system, a large scale of reaction equipments is required for mass-producing. For example, 250 g of baker's yeast, 375 g of glucose and 2.5 liters of water are required in the reaction of 25 g of substrate.

(3) As a large volume of baker's yeast and water are contained in a system, it takes long time for removing the baker's yeast and for extracting the objective from water.

(4) Generally, in the case of asymmetric reduction with baker's yeast, the product has different optical purity in each reaction process.

(5) Only one of antipodes is obtained. In this case, only one R-compound is obtained.

Therefore, Mori et al tried asymmetric reduction of substrate containing S atoms in the molecule, which is able to become equivalent in organic chemical conversion, with high temperature yeast (pichia terricola) to obtain an optically purified hydroxy ester (Enzyme Function and Precision Organic Synthesis, published by C. M. C., pp 60-61 (1984). In this case, there are industrially troublesome disadvantages as follows.

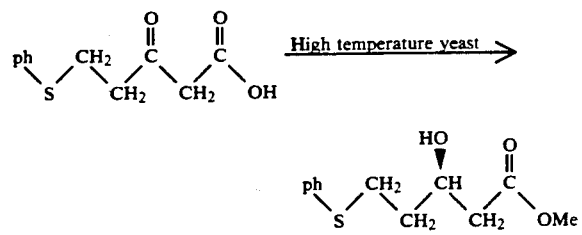

(1) As described above, yeast is used in this process, so that the concentration of substrate is very low and the production process is very complicate.

(2) The preparation of starting substrate is difficult, and methyl 3-hydroxypentanate should be again obtained after the asymmetric reduction. Accordingly, the process can not be industrially utilized.

(3) The method provides only one of the antipodes.

Furthermore, Hasegawa et al obtained methyl R-3-hydroxypentanate from pentanic acid by oxidation reaction in the presence of *Candida rugosa*. However, there are the following disadvantages (J. Hasegawa et al, J. Ferment. Technol., 61, 37 (1983)).

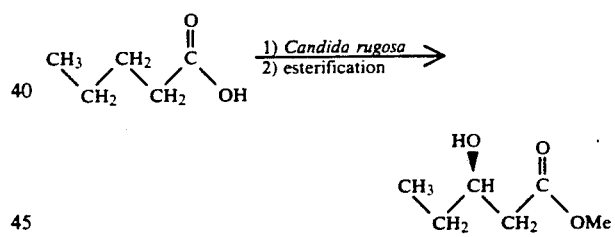

(1) The obtained product has a low optical purity of 83–93% ee. For obtaining a substance having high optical purity, the material is led to the ester of 3,5-dinitro benzoic acid, and then a preferential crystallization method which is primitive and inefficient should be used.

(2) As described above, the concentration of the substrate is very low and the operation of purification is very troublesome.

(3) The method provides only one of antipodes.

Firstly, the conventional methods as described above can not provide a substance having high purity. Otherwise, the substance is obtained through complex processes. Secondly, as the concentration of the substrate in the reaction system is low and the operation of purification is extremely troublesome, the methods are unsuitable for the production of an industry level. Thirdly, only one of antipodes can not be obtained, and different methods must be studied for obtaining the other antipode. All of the above reports do not refer to substrates of esters having long alkyl chains and to their effect.

SUMMARY OF THE INVENTION

The inventors of the present invention found the process for efficiently producing the optical active compounds of alkyl 3-hydroxybutanate in Japanese Patent Application 63-256952/1986, and they further carried out research for obtaining a process for efficiently producing a specified optically active compound.

Namely, the present invention provides a process for producing optically active alcohols and optically active esters represented by the general formula:

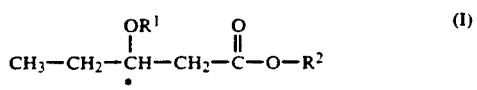
(I)

wherein $R^1$ is hydrogen or acyl of 2-20 carbon atoms, $R^2$ is alkyl, alkenyl or alkynyl of 3-40 carbon atoms, and the carbon indicated by * is an asymmetric carbon atom.

Further, the present invention provides a process for producing an optically active compound which comprises reacting an ester with an (R,S)-compound represented by the general formula:

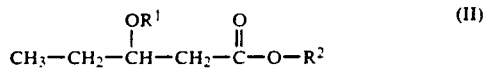
(II)

wherein $R^1$ is hydrogen or acyl of 20-20 carbon atoms, and $R^2$ is alkyl,alkenyl or alkynyl of 3-40 carbon atoms, under substantially anhydrous conditions and in the presence of a hydrolase to effect a transesterification reaction between the ester and the (R,S)- compound, obtaining a mixture enriched in either the R- or S-compound and resolving the mixture into the corresponding optically active R- or S-alcohol and the ester.

In the process of the present invention, the reaction is conducted under substantially anhydrous conditions. This process does not require the use of a small amount of water or a lower alcohol instead of water, so that the esters for transesterification or the esters obtained are not hydrolyzed. No side reaction occurs with a formation of undesired esters. The enzyme is easily separated after the reaction and re-used. Furthermore, since the reaction of the present invention is conducted under substantially anhydrous conditions, the reaction zone can be kept free from contamination of undesired microorganisms. There is no necessity for preparing a special equipment, antiseptics, sterilization treatment, etc.. It is possible to conduct the reaction in an open system. Further, the reaction may be conducted in the same or high substrate concentration in comparison with common organic synthetic reactions.

DETAILED DESCRIPTION OF THE INVENTION

The following description illustrates the present invention more specifically.

In the present invention, the (R,S)-alcohols of the raw materials can be easily produced.

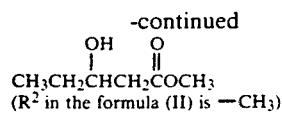
(III)

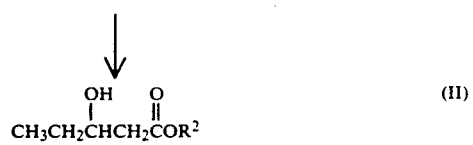
(IV)
($R^2$ in the formula (II) is $-CH_3$)

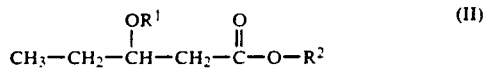
(II)

Namely, a reductant represented by sodium borohydride and the like is reacted with the compound (III) which is industrially available and the compound (IV) is obtained. Then, the ester moiety of the compound (IV) is exchanged to obtain the (R,S)-compound (II). Further, (R,S)-compounds represented by the general formula (II) are obtainable by reacting several kinds of ester of bromoacetic acid (V) and propionaldehyde (VI) in the presence of zinc.

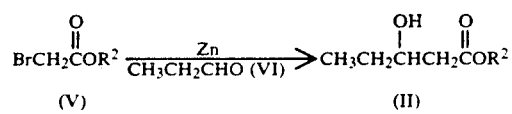

The other common chemical methods of organic synthesis can be used for producing the above compounds by many kinds of processes.

It is also enough to use esters for transesterification which are commercially available easily. Methyl propionate, ethyl butyrate, ethyl stearate, trichloroethyl ethyl laurate, butyl laurate, ethylene glycol diacetate, etc. are usable. Preferably, fatty acid vinyl esters and triglycerides such as vinyl acetate, vinyl caproate, vinyl laurate, triacetin, tripropionin, tributyrin, tricaproin, tristearin, trilaurin, trimyristin, triolein, etc. can be exemprified as the esters.

As the enzyme which is used in the present invention, a lipase, lipoprotein lipase, esterase, or the like is preferable. The enzyme has the ability to catalyse a transesterification reaction preferentially between the R- or S-compound and the ester when the enzyme is used with the (R,S)-compound, and the enzyme can be used regardless its class. The following table shows commercially available enzymes that can be used in the present reaction.

TABLE

| Trade name | Origin | Seller or Maker |
|---|---|---|
| Lipase AP | Aspergillus niger | Amano Pharmaceutical Co., Ltd |
| Lipase M | Mucor javanicus | Amano Pharmaceutical Co., Ltd |
| Lipase P | Pseudomonas fluorescens | Amano Pharmaceutical Co., Ltd |
| Lipase CES | Pseudomonas sp | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine Pancreas | Sigma Chemical Co. |
| Lipase VIII | Geotrichum Candidum | Sigma Chemical Co. |
| Lipase X | Rhizopus delamar | Sigma Chemical Co. |
| Lipase | Chromobacterium Viscosum | Toyo Jozo Co., Ltd. |
| Palatase A | Aspergillus niger | Novo Industi A/S |
| Lipase | Rhizopus niveus | Nagase Biochemi- |

TABLE-continued

| Trade name | Origin | Seller or Maker |
|---|---|---|
| Lipase B | Pseudomonas fragi | cals. Ltd. Sapporo Beer Co. |

In addition to these enzymes, the enzymes produced from microorganisms which produce the enzymes having the above ability can be used regardless of their species and genus. As such microorganisms, the genra Arthrobacter, Acromobacter, Alcaligenes, Aspergillus, Chromobacterium, Candida, Mucor, Pseudomonas, Rhizopus, etc. can be exemplified.

The process for producing the optically active compound of the present invention is described more detailedly. The reaction is conducted by mixing an (R,S)-compound with an ester, preferably a fatty acid vinyl ester or a triglyceride, and contacting efficiently the mixture with an enzyme. The (R,S)-compound used in this process and the ester such as the fatty acid vinyl ester or the triglyceride can be used without any particular treatments. When the (R,S)-compound is slightly soluble in the ester, an organic solvent such as heptane or toluene can be added. The reaction temperature is suitably 0° to 100° C., it is changeable by the class of the enzyme, and especially preferably 30° to 45° C. The reaction time is changeable by the class of the substrate for periods of 5 to 2000 hours. The reaction time can be shortened by changing the reaction temperature, the enzyme class and the substrate concentration.

The (R,S)-compound which is a substrate and the ester are suitably mixed in the ratio 1:0.5 to 1:2 by mole.

After the transesterification reaction as described above, the enzyme can be removed by conventional filter operation and used again, as it is. Otherwise, the reaction can be repeated by using the enzyme which is adsorbed and fixed on a hydrophobic resin and the like. The reactant which is the filtrate can be separated into an optically active alcohol and an optically active ester which is an antipode of the alcohol, respectively, for instance by distillation or column chromatography. The obtained optically active ester is hydrolyzed to derive the optically active alcohol which is an antipode of the said optically active alcohol. The optically active alcohols have a little different optical purity based on the kinds of $R^2$, and based on optical active type of R or S. These alcohols can be obtained by reacting again with an enzyme as described in the following Examples or by transesterification of the compound obtained in high optical purity with a common chemical method of organic synthesis.

However, the ester part of $R^2$ in the formula (II) of the (R,S)-compound used in the present invention preferably has 3 or more carbons, and particularly 1,1-dimethylethyl is preferred. As shown in Examples, when the enzyme reaction is conducted by using the (R,S)-compound wherein $R^2$ is ethyl as substrate, the optical purity of the optically active S- and R- compounds obtained in Example 1 is 50% ee and 80% ee, respectively. On the other hand, when the enzyme reaction is conducted by using the (R,S)-compound wherein $R^2$ is 1,1-dimethylethyl as substrate, the optical purity of the optically active S- and R- compounds obtained in Example 4 is 75% ee and 100% ee, respectively. The latter case shows very high selectivity.

The optically active alcohols obtained by the above described processes are represented by the following.

When $R^1$ in the formula (I) is hydrogen, there are optically active methyl 3-hydroxypentanate,
optically active ethyl 3-hydroxypentanate,
optically active propyl 3-hydroxypentanate,
optically active butyl 3-hydroxypentanate,
optically active pentyl 3-hydroxypentanate,
optically active hexyl 3-hydroxypentanate,
optically active heptyl 3-hydroxypentanate,
optically active octyl 3-hydroxypentanate,
optically active nonyl 3-hydroxypentanate,
optically active decyl 3-hydroxypentanate,
optically active undecyl 3-hydroxypentanate,
optically active dodecyl 3-hydroxypentanate,
optically active tridecyl 3-hydroxypentanate,
optically active 1-methylethyl 3-hydroxylpentanate,
optically active 1-methylpropyl 3-hydroxypentanate,
optically active 2-methylpropyl 3-hydroxypentanate,
optically active 1,1-dimethylethyl 3-hydroxypentanate,
optically active 1-methylbutyl 3-hydroxypentanate,
optically active 2-methylbutyl 3-hydroxypentanate,
optically active 3-methylbutyl 3-hydroxypentanate,
optically active 1,1-dimethylpropyl 3-hydroxypentanate,
optically active 1-methylpentyl 3-hydroxypentanate,
optically active 2-methylpentyl 3-hydroxypentanate,
optically active 3-methylpentyl 3-hydroxypentanate,
optically active 4-methylpentyl 3-hydroxypentanate,
optically active 1,1-dimethylbutyl 3-hydroxypentanate,
optically active 1-methylhexyl 3-hydroxypentanate,
optically active 2-methylhexyl 3-hydroxypentanate,
optically active 3-methylhexyl 3-hydroxypentanate,
optically active 4-methylhexyl 3-hydroxypentanate, and
optically active 5-methylhexyl 3-hydroxypentanate.

When $R^1$ in the formula (I) is acyl of 2-20 carbon atoms, there are
optically active methyl 3-acetyloxypentanate,
optically active methyl 3-propionyloxypentanate,
optically active methyl 3-butyryloxypentanate,
optically active methyl 3-valeryloxypentanate,
optically active methyl 3-hexanoyloxypentanate,
optically active methyl 3-heptanoyloxypentanate,
optically active methyl 3-octanoyloxypentanate,
optically active methyl 3-nonanoyloxypentanate,
optically active ethyl 3-acetyloxypentanate,
optically active ethyl 3-propionyloxypentanate,
optically active ethyl 3-butyryloxypentanate,
optically active ethyl 3-valeryloxypentanate,
optically active ethyl 3-hexanoyloxypentanate,
optically active ethyl 3-heptanyloxypentanate,
optically active ethyl 3-octanoyloxypentanate,
optically active ethyl 3-nonanoyloxypentanate,
optically active propyl 3-acetyloxypentanate,
optically active propyl 3-propionyloxypentanate,
optically active propyl 3-butyryloxypentanate,
optically active propyl 3-valeryloxypentanate,
optically active propyl 3-hexanoyloxypentanate,
optically active propyl 3-heptanoyloxypentanate,
optically active propyl 3-octanoyloxypentanate,
optically active propyl 3-nonanoyloxypentanate,
optically active butyl 3-propionyloxypentanate,
optically active butyl 3-butyryloxypentanate,
optically active butyl 3-valeryloxypentanate,
optically active butyl 3-hexanoyloxypentanate,
optically active pentyl 3-propionyloxypentanate,
optically active pentyl 3-butyryloxypentanate,
optically active pentyl 3-valeryloxypentanate,
optically active pentyl 3-hexanoyloxypentanate, optically active 1,1-dimethylethyl 3-acetyloxypentanate, optically active 1,1-dimethylethyl 3-propionyloxypentanate, optically active 1,1-dimethylethyl 3-butyryloxypentanate, optically active 1,1-dimethylethyl 3-valeryloxypentanate, optically active 1,1-dimethylethyl 3-hexanoyloxypentanate, optically active 1,1-dimethylethyl 3-heptanoyloxypentanate, optically active 1,1-dimethylethyl 3-octanoyloxypentanate, and optically active 1,1-dimethylethyl 3-nonanoyloxypentanate.

The merits of the present invention are as follows.

(1) Unnecessary hydrolysis of esters scarcely occurs because the transesterification reaction is conducted under substantially anhydous conditions.

(2) The enzyme can be easily recovered and re-used.

(3) No special equipment and materials are used because the reaction can be performed under the conditions of relatively lower temperatures and an open system.

(4) Optically active substances having high purity are obtained by a one-step reaction.

(5) In spite of the biochemical reaction, the substrate concentration can be increased and big reaction vessels are unnecessary, because a buffer solution and the like are not required in the reaction. As shown in Example 6, the scale-up of production is possible and it is industrially useful.

(6) The compound (I) of the present invention is useful as starting materials for physiological active materials and functional materials.

For example, the compound (I) is useful as starting materials of threo-4-methyl-3-heptanol which is a constitutent element of pheromone of Scolytus multistriatus (G. Frater, Helv. Chim. Acta, 62, 2829 (1979)) and (4s, 6s, 7s)-sericornin which is pheromone of cigarette beetle *Lasioderma serricorne* F (K. Mori et al, Tetrahedron, 41, 3423).

DESCRIPTION OF PREFERRED EMBODIMENTS

The following Examples illustrate this invention more specifically. The optical purity in Examples, is determined by the following method: after the optically active compounds obtained was derived to ethyl 3-hydroxypentanate, NMR was used in the presence of En(hfc)$_3$ as a shift agent.

EXAMPLE 1

Optical resolution of ethyl 3-hydroxypentanate (i) The mixture of 9.6 g of ethyl ($\pm$)-3-hydroxypentanate, 21.8 g of tributyrin and 1.5 g of enzyme (produced by Amano Pharmaceutical Co. Ltd., lipase "Amano P") was stirred for 80 hours at 38° C. After the enzyme was removed by suction filtration, the filtrate was chromatographed over silica gel, and the purified 2.0 g of ethyl R-(+)-3-butyryloxypentanate, $[\alpha]_D^{32} = +7.7°$ (C=0.79, CHCl$_3$), and 2.8 g of ethyl S-(+)-3-hydroxypentanate, $[\alpha]_D^{32} = +16.6°$ (C=1.12, CHCl$_3$), were obtained. By using Eu(hfc)$_3$ as a shift agent, the optical purity of ethyl S-(+)-3-hydroxypentanate was tested. The enanthio ratio was 3:1 and the purity was about 50% ee.

$^1$H-NMR: 4.18 (q, 2H); 3.98–3.9(m, H-C(3)); 3.1–2.9(br, HO); 2.52(dxd, J(2, 2')=18. J(2, 3)=3, H-C(2)); 2.4(dxd, J(2, 2')=18. J(2', 3)=9. H'-C(2)); 1.6–1.44(m, 2H-C(4)); 1.28(t, CH$_3$CH$_2$O); 0.97(t, 3H-C(5)).

(ii) The mixture of 1.9 g of ethyl R-(+)-3-butyryloxypentanate, 16 ml of 1,2-dichloroethane, 16 ml of ethanol and 0.3 ml of sulfuric acid was refluxed for 40 hours, water and ethyl acetate was added and the mixture was stirred. The separated organic layer was washed with a saturated aqueous solution of sodium bicarbonate and then with water, and dried on anhydrous magnesium sulfate. The solvent was distilled away, and 1.0 g crude product was obtained. The crude product was chromatographically purified, and 0.63 g of ethyl R-(−)-3-hydroxypentanate. $[\alpha]_D^{24} = -29.7°$ (C=0.90, CHCl$_3$). As described above, the optical purity of the obtained compound was tested by using Eu(hfc)$_3$ as a shift agent. It was 88% ee. Moreover, the formulation of the above compounds was supported well by their NMR charts.

EXAMPLE 2

Optical resolution of methyl 3-hydroxypentanate

The mixture of 9.3 g of methyl ($\pm$)-3-hydroxypentanate, 20.1 g of tripropionin and 1.3 g of lipase "Amano P" was stirred for 70 hours at 38° C. After the enzyme was removed by suction filtration, the filtrate was chromatographed over silica gel, and the purified 1.8 g of methyl R-(+)-3-propionyloxypentanate and 2.4 g of methyl S-(+)-3-hydroxypentanate were obtained. Moreover, the formulation of the above compounds was supported well by their NMR charts.

EXAMPLE 3

Optical resolution of propyl 3-hydroxypentanate (i) The mixture of 10.0 g of propyl ($\pm$)-3-hydroxypentanate, 19.0 g of tributyrin and 1.5 g of lipase "Amano P" was stirred for 64 hours at 38° C. After the enzyme was removed by suction filtation, the filtate was chromatographed over silica gel, and the purified 5.2 g of propyl R-(+)-3-butyryloxypentanate and 2.6 g of propyl S-(+)-3-hydroxypentanate, $[\alpha]_D^{28} = +18.6°$ (C=1.10 CHCl$_3$), were obtained. The formulation of the above compounds was supported well by their NMR charts.

(ii) Using the same method as in Example 1 (ii), the above propyl R-(+)-3-butyryloxypentanate was converted into ethyl R-(−)-3-hydroxypentanate by using 1,2-dichloroethane, ethanol and sulfuric acid. $[\alpha]_D^{29} = -30.3°$ (C=1.03, CHCl$_3$). As described in Example 1 (i), the optical purity of the obtained propyl R-(+)-3-butyryloxypetanate was tested by using Eu(hfc)$_3$ as a shift agent and the value was 90% ee.

(iii) Using the same method as in Example 1 (ii), propyl S-(+)-3-hydroxypentanate obtained in (i) was converted into ethyl S-(+)-3-hydroxypentanate by using 1,2-dichloroethane, ethanol and sulfuric acid. $[\alpha]_D^{28} = +21.1°$ (C=1.69, CHCl$_3$). As described in Example 1 (i), the optical purity of the obtained ethyl S-(+)-3-hydroxypentanate was tested by using Eu(hfc)$_3$ as a shift agent and the value was 63% ee, therefore, the optical purity of propyl S-(+)-3-hydroxypentanate obtained in (i) was 63% ee.

EXAMPLE 4

Optical resolution of 1,1-dimethylethyl 3-hydroxypentanate (i) The mixture of 6.0 g of 1,1-dimethylethyl (±)-3-hydroxypentanate, 14.5 g of tricaproin and 1.5 g of lipase "Amano P" was stirred for 120 hours at 38° C. After the enzyme was removed by suction filtration, the filtrate was chromatographed over silica gel, and the purified 3.4 g of 1,1-dimethylethyl R-(+)-3-hexanoyloxypentanate, $[\alpha]_D^{21} = +8.9°$ (C=0.88, CHCl$_3$), and 2.5 g of 1,1-dimethylethyl S-(+)-3-hydroxypentanate, $[\alpha]_D^{20} = +23.0°$ (C=0.96, CHCl$_3$) were obtained. The formulation of the above compounds was supported well by their NMR charts.

(ii) Using the same method as in Example 1 (ii), the above 1,1-dimethylethyl R-(+)-3-hexanoyloxypentanate was converted into ethyl R-(−)-3-hydroxypentanate by using 1,2-dichloroethane, ethanol and sulfuric acid. $[\alpha]_D^{25} = -35.6°$ (C=1.07, CHCl$_3$). As described in Example 1 (i), the optical purity of ethyl R-(−)-3-hydroxypentanate was tested and the value was 100% ee, therefore, 1,1-dimethylethyl R-(+)-3-hexanoyloxypentanate obtained in (i) was 100% ee.

(iii) Using the same method as in Example 1 (ii), 1,1-dimethylethyl S-(+)-3-hydroxypentanate obtained in (i) was converted into ethyl S-(+)-3-hydroxypentanate by using 1,2-dichloroethane, ethanol and sulfuric acid. $[\alpha]_D^{28} = +25.2°$ (C=1.17, CHCl$_3$). As described in Example 1 (i), the optical purity of the obtained compound was tested by using Eu(flc)$_3$ as a shift agent and the value was 75% ee, therefore, the optical purity of 1,1-dimethylethyl S-(+)-3-hydroxypentanate obtained in (i) was 75% ee.

EXAMPLE 5

The 2nd enzyme reaction of 1,1-dimethylethyl S-(+)-3-hydroxypentanate

The mixture of 1.5 g of 1,1-dimethylethyl S-(+)-3-hydroxypentanate (75% ee) obtained in Example 4, 3.5 g of tricaproin and 0.5 g of lipase "Amano P" was stirred for 100 hours at 38° C. After removing the enzyme by suction filtration, the filtrate was chromatographed over silica gel and purified. 0.2 g of 1,1-dimethylethyl R-(+)-3-hexanoyloxypentanate and 0.6 g of 1,1-dimethylethyl S-(+)-3-hydroxypentanate were obtained.

Using the same method as in Example 1 (ii), the above 1,1-dimethylethyl S-(+)-3-hydroxypentanate was converted into ethyl S-(+)-3-hydroxypentanate by using 1,2-dichloroethane, ethanol and sulfuric acid. $[\alpha]_D^{25} = +34.2°$ (C=1.00, CHCl$_3$). As described in Example 1 (i), the optical purity of the obtained compound was 100% ee, therefore, the optical purity of the above 1,1-dimethylethyl S-(+)-3-hydroxypentanate was 100% ee.

As described above, by repeating two times the enzyme reaction, it is found that optically active alkyl 3-hydroxypentanate having optical purity can be obtained.

EXAMPLE 6

Optical resolution of 1,1-dimethylethyl 3-hydroxypentanate (i) The mixture of 369.6 g of 1,1-dimethylethyl (±)-3-hydroxypentanate, 288 g of vinyl laurate, 50 g of lipase "Amano P" was stirred for 20 hours at 25° C. After the enzyme was removed by suction filtration, the filtrate was purified by distillation, and 424.7 g of 1,1-dimethylethyl R-(+)-3-dodecanoyloxy-pentanate, and 140.9 g of 1,1-dimethylethyl S-(+)-3-hydroxypentanate, $[\alpha]_D^{20} = +25.0°$ (C=1.00, CHCl$_3$) were obtained. b.p. 94° C. at 42 mmHg. The formulation of the above compounds was supported well by their NMR charts.

(ii) Using the same method as in Example 1 (ii), the above 1,1-dimethylethyl R-(+)-3-dodecanoyloxypentanate was converted into ethyl R-(−)-3-hydroxypentanate by using 1,2-dichloroethane, ethanol and sulfuric acid. $[\alpha]_D^{25} = -33.6°$ (C=1.05, CHCl$_3$). As described in Example 1 (i), the optical purity of ethyl R-(−)-3-hydroxypentanate was tested and the value was 94.4% ee, therefore, 1,1-dimethylethyl R-(+)-3-dodecanoyloxypentanate obtained in (i) was 94.4% ee.

(iii) Using the same method as in Example 1 (ii), 1,1-dimethylethyl S-(+)-3-hydroxypentanate obtained in (i) was converted into ethyl S-(+)-3-hydroxypentanate by using 1,2-dichloroethane, ethanol and sulfuric acid. $[\alpha]_D^{25} = +27.4°$ (C=0.99, CHCl$_3$). As described in Example 1 (i), the optical purity of the obtained compound was tested by using Eu(flc)$_3$ as a shift agent and the value was 82.7% ee, therefore, the optical purity of 1,1-dimethylethyl S-(+)-3-hydroxypentanate obtained in (i) was 82.7% ee.

We claim:

1. A process for producing an optically active compound which comprises reacting an ester selected from the group consisting of a fatty acid vinyl ester and a triglyceride with an (R,S)-compound represented by the general formula:

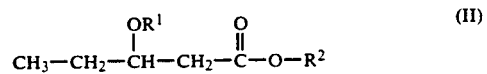

wherein R$^1$ is hydrogen or acyl of 2–20 carbon atoms, and 1,1-dimethylethyl under substantially anhydrous conditions and in the presence of a hydrolase to effect a transesterification reaction between the ester and the (R,S)-compound, obtaining a mixture enriched in either the R- or S-compound and resolving the mixture into the corresponding optically active R- or S-alcohol and the ester having the general formula:

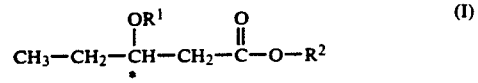

wherein R$^1$ is hydrogen or acyl of 2–20 carbon atoms, R$^2$ 1,1-dimethylethyl, and the carbon indicated by * is an asymmetric carbon atom.

2. A process according to claim 1 wherein the ester is a triglyceride.

3. A process according to claim 1 wherein the ester used is a fatty acid vinyl ester.

4. A process according to claim 1 wherein the hydrolase is lipase.

5. A process according to claim 1 wherein the hydrolase is lipase which is derived from Pseudomonas sp.